United States Patent [19]

Garrison et al.

[11] 4,223,014

[45] Sep. 16, 1980

[54] SPRAY IMMUNIZATION OF FISH

[75] Inventors: Robert L. Garrison; Rowan W. Gould; Patrick J. O'Leary; John L. Fryer, all of Corvallis, Oreg.

[73] Assignee: The United States of America as represented by the Secretary of the Interior, Washington, D.C.

[21] Appl. No.: 903,430

[22] Filed: May 8, 1978

Related U.S. Application Data

[63] Continuation of Ser. No. 769,128, Feb. 16, 1977, abandoned.

[51] Int. Cl.² ............... A61K 39/02; A61K 39/12; A61K 9/12
[52] U.S. Cl. ............................. 424/92; 424/46; 424/89
[58] Field of Search ............................ 424/89, 92, 46

[56] References Cited

U.S. PATENT DOCUMENTS

| | | | |
|---|---|---|---|
| 2,140,409 | 12/1938 | Sterling | 128/253 |
| 2,782,975 | 2/1957 | Bird | 141/392 |
| 2,924,219 | 2/1960 | Wershaw | 128/260 |
| 2,952,585 | 9/1960 | Heller | 167/78 |
| 3,435,112 | 3/1969 | Kuhns et al. | 424/89 |
| 3,492,400 | 1/1970 | Klontz | 424/92 |
| 3,501,770 | 3/1970 | Gale | 424/89 |
| 3,577,523 | 5/1971 | Stolar et al. | 424/89 |
| 3,608,066 | 9/1971 | Illartein | 424/92 |
| 3,755,557 | 8/1973 | Jacobs | 424/46 |
| 3,862,313 | 1/1975 | Fryer et al. | 424/92 |
| 4,009,259 | 2/1977 | Ament et al. | 424/89 |

OTHER PUBLICATIONS

J. L. Fryer et al., Development of Bacterins and Vaccines for Control of Infectious Diseases in Fish, Dec. 1977, Oregon State University Sea Grant College Program, Publication No. ORESU-T-77-012, pp. 1-10.
Cosmetics:Science & Technology, M. S. Balsam et al., p. 446, (Chap. 26), 1972, Wiley & Sons.
L. W. Harrell et al., Vet. Bull., 46, No. 10, No. 5437, (1976), Aqua–Culture, (1975), 6, 3, 211-219.
J. O. Cisar et al., Infect. & Immun., Feb. 1974, pp. 236-243.
K. D. Spence et al., Can. J. of Microbiol., vol. 11, No. 3, Jun. 1965, pp. 397-405.
L. W. Harrell et al., Aquaculture, (1976), 363-370.
R. D. Gunnels et al., Am. J. Vet. Res., 37, 6, (1976), 737-740.

*Primary Examiner*—Donald G. Daus
*Assistant Examiner*—M. C. Eakin
*Attorney, Agent, or Firm*—Gersten Sadowsky; Donald A. Gardiner

[57] ABSTRACT

A method for immunizing fish against disease by spraying with vaccine or bacterin.

7 Claims, No Drawings

SPRAY IMMUNIZATION OF FISH

This is a continuation of application Ser. No. 769,128, filed Feb. 16, 1977, now abandoned.

BACKGROUND OF THE INVENTION

A number of vaccines have been developed for the control of diseases in fish, as illustrated for example, in U.S. Pat. Nos. 3,492,400 to Klontz and 3,862,313 to Fryer et al. In the past such vaccines have been administered by peritoneal injection or by incorporation in food or water. More recently vacuum infiltration (rapid pressure change) and hyperosmotic vaccine dips have been proposed. Peritoneal injections of large antigenic masses have been highly effective; however, when applied to large numbers of fish this method is cumbersome and costly. Incorporation of vaccine into the food or water is probably the most desirable system since it is relatively simple and economical. However, its effectiveness has been demonstrated in only a limited number of diseases. In addition the duration of protection by this method has been much shorter than that obtained by injection. The newer techniques of vacuum infiltration and hyperosmotic vaccine dips lend themselves to vaccination of small fish, but would be time consuming and costly when applied to larger fish. Unless the disease causing organism is constantly present to reinforce immunity, or if for any reason immunity is diminished, re-vaccination of larger fish with these techniques would be inefficient.

Spray vaccination will be especially useful where previously vaccinated fish are not constantly exposed to the disease causing agent. In this situation, unreinforced immunity may significantly decrease with time. For example, if salmon are vaccinated against *V. anguillarum* as fry, hatchery rearing periods as long as one year or more without natural contact with the target agent may lead to a reduction in protection. Before releasing the fish from the hatchery, the spray technique of this invention could be employed to revaccinate them, or possibly to supply a booster shot.

The present invention comprises an antigenic material useful for immunizing fish against disease and a spray method for administering the antigenic material to the fish.

Accordingly it is an object of the invention to provide an antigenic material for the immunization of fish against disease.

Another object of the invention is to provide a method for administering the antigenic material to fish efficiently and at low cost.

Another object is to provide a method for administering the antigenic material to the fish by means of a spray.

A further object of the invention is to provide a pressure spray method for immunizing fish employing antigenic material containing an absorbent.

Yet a further object of the invention is to employ an antigenic material containing an abrasive for administration to fish by means of a pressure spray.

DESCRIPTION OF THE INVENTION

Basically, our invention consists in removing the fish from water by a dip net, and while suspended in the air spraying it with antibody material. Another method is to cause the fish to pass through a trough and to spray the fish as they pass through. Ordinary spray or sandblasting guns may be employed to deliver the spray. The air pressure used must be sufficient to cause the spray to penetrate and to produce within the body of the fish the humoral antibody response characteristic of the vaccine or bacterin. Ordinarily any pressure up to 90 psi is satisfactory, with the higher portion of a range of about 80 to 90 psi being more desirable. Too high a pressure is to be avoided since it may cause physical damage.

The antigenic material employed may consist of exotoxins, killed, or attenuated microorganisms. We have found bacterins comprising formalin killed bacteria to be highly useful, but other vaccines and bacterins may be employed.

EXAMPLE 1

A labelled vaccine of formalin killed *Vibrio anguillarum* bacterin attached to yellow fluorescent dye, consisting of 100 milligrams dry weight killed *V. anguillarum* (LS-1-74) per 1 gram dye was employed in this experiment. The dye and wet bacteria was thoroughly mixed, lyophilized overnight at 100 micro Hg pressure, and ground in a mortar. A fifty fish group of coho salmon (*Oncorhynchus kisutch*) at 30/lb. were suspended in a dip net and sprayed with the dry powder bacterin at a distance at 12–15 inches to coat the fish. As a control, a similar group of coho salmon was sprayed with a blue fluorescent dye which contained no bacterin. Both groups were held at 13° C. for 27 days. Individual titers against *V. anguillarum* (LS-1-74) were determined employing the micro titer technique against 5 fish in each group. A geometric mean titer of 1:196 was found in the vaccinated fish and zero titer in the unvaccinated group. The remaining fish in each group were exposed to an artificial water borne challenge to *V. anguillarum* LS-1-74. An 86% mortality resulted in the unvaccinated group and only 2% mortality in the vaccinated group.

EXAMPLE 2

A series of tests were run to examine various parameters of the spray vaccination technique. Different concentrations of formalin killed *V. anguillarum* bacterin were attached to fluorescent dye, as described in Example 1, the concentrations ranging from 1 microgram to 100 milligrams bacteria/gram dye.

Also, employed were water dispersions of the bacterin/dye formulation, a killed TGY culture of *V. anguillarum*, and a bacterin mixture with alumina.

Groups of 50 cold brand marked coho salmon were sprayed at 90 psi with each formulation, and one group was sprayed with a dye preparation without bacterin as a control.

Table 1 gives the geometric mean of the individual titers and the mortality suffered by the sample.

TABLE 1

Comparison of effectiveness of various concentrations and compositions of *Vibrio anguillarum* LS-1-74 bacterin spray preparations.

| Run | Preparation Constitutents | Geometric mean individual titers against *Vibrio anguillarum* LS-1-74 (five fish sample) | Mortality suffered in an artificial challenge to *Vibrio* ($2 \times 10^6$ bacteria/ml in challenge tank) |
|---|---|---|---|
| 1 | Blue fluorescent | | |

TABLE 1-continued

| | | | |
|---|---|---|---|
| | dye Control 50:50 H₂O + 1 microgram bacterin per gram | 1:2 | 37/47 79% |
| 2 | of yellow fluorescent dye 10 microgram bacterin per gram | 1:5 | 24/43 56% |
| 3 | of yellow fluorescent dye 100 microgram bacterin per gram | 1:21 | 31/42 74% |
| 4 | of yellow fluorescent dye 1 milligram bacterin per gram | 1:21 | 25/45 56% |
| 5 | of yellow fluorescent dye 10 milligram bacterin per gram | 1:32 | 3/50 6% |
| 6 | of yellow fluorescent dye | 1:147 | 0/45 0% |
| 7 | 10 milligram bacterin per gram of alumina | 1:147 | 1/46 2% |
| 8 | 100 milligram bacterin per gram of yellow fluorescent dye 50:50 | 1:256 | 0/45 0% |
| 9 | H₂O + 100 milligram bacterin per gram of yellow fluorescent dye | 1:256 | 0/47 0% |
| 10 | 96 hr., 30° C. TGY culture of *v. anguillarum* LS-1-74 killed with 0.3% formalin | 1:48 | 2/44 5% |

The bacterin of Run 10 was prepared by innoculating a Trypton Glucose Yeast (TGY) broth with *V. anguillarum* LS-1-74 and allowed to grow at 30° C. for 96 hours. 0.3% formalin was added and the culture allowed to stand overnight. The preparation was checked for sterility and then sprayed on a group of 50 coho salmon. Table 1 shows that the TGY sprayed fish had an antibody titer greater than the 1 mg/gm dye preparation of Run 5 and had a similar protection percentage.

A comparison of Runs 6 and 7 shows that the substitution of alumina for yellow fluorescent dye did not affect the results.

EXAMPLE 3

This experiment was carried out to determine the titers elicited by spraying polyvalent whole cell bacteria. Each vaccine tested consisted of 0.3% formalin killed *Aeromonas salmonicida* AS-SS-70, *V. anguillarum* LS-1-74 and *V. anguillarum* MSC-2-75. The spray preparations consisted of 500 ml. deionized water, 50 grams of ground pumice (grade FFF) and 1 gram wet-weight of each included bacterin type. Approximately 400 micrograms (dry weight) of each included bacterin per ml. was the concentration. The purpose of the pumice was to scarify the fish with the hope of thereby increasing the titer. Four vaccines were prepared consisting of AS-SS-70, AS-SS-70 and LS-1-74, AS-SS-70 plus LS-1-74 and MS-275, and LS-1-74 plus MSC-2-75. Fish samples of 50 coho salmon each were sprayed with each of the four vaccines and with a control containing no bacterin. By calculation, each individual fish received about 0.5 ml of preparation. The fish were held at 13° C. for 29 days. Titers were then taken on five individual fish from each group. The results are shown in the following table.

TABLE 2

Titers against constituent antigens of various combinations of bacterins applied by spray injection. All titers reported are geometric means of individual determinations on five fish samples.

| Titer Antigen | NONE CONTROL | AS-SS-70[1] | AS-SS-70 LS-1-74[2] | AS-SS-70 LS-1-74 MSC-2-75[3] | LS-1-74 MSC-1-75 |
|---|---|---|---|---|---|
| AS-Sil-67[4] | 1:55 | 1:64 | 1:64 | 1:147 | 1:64 |
| LS-1-74 | 0 | 0 | 1:16 | 1:28 | 1:16 |
| MSC-2-75 | 0 | 0 | 0 | 1:169 | 1:64 |

[1] AS-SS-70 - *Aeromonas salmonicide* - 1970 South Santiam isolate - virulent
[2] LS-1-74 - *Vibrio anguillarum* - 1974 Lint Slough isolate - fast grower
[3] MSC-2-75 - *Vibrio anguillarum* - 1975 Marine Science Center, Yaquina Bay isolate - slow grower
[4] AS-Sil-67 - *Aeromonas salmonicide* - 1967 Siletz isolate - avirulent. Since AS-SS-70 autoagglutinates, the non-autoagglutinating, antigenically similar, avirulent AS-Sil-67 was used as the indicator antigen instead.

The remaining fish were subjected to an artificial water-borne furunculosis challenge. The combined lots not receiving furunculosis bacterin suffered an 85% mortality while the combined lots receiving the bacterin suffered a 72% mortality. The difference was significant at the 95% confidence interval.

EXAMPLE 4

Bentonite was added to vaccine preparations in an attempt to increase antibody titer in the sprayed fish. A late stationary phase culture of *V. anguillarum* LS-1-74 was grown at 30° C. in BHI and divided into three aliquat parts. Groups of approximately 30 coho salmon (20/lb.) were sprayed with the following preparations.

1. Uninoculated BHI (control).
2. Late stationary phase culture of *V. anguillarum* LS-1-74.
3. Late stationary phase culture of *V. anguillarum* LS-1-74 plus 0.15% bentonite (w/v).
4. Late stationary phase culture of *V. anguillarum* LS-1-74 plus 0.15% bentonite (w/v) adjusted to a 9.0 pH with 5 N NaOH.

At the end of a 30 day period the geometric mean of the titers were as follows:

| GROUP | TITER |
|---|---|
| 1 | 0 |
| 2 | 1:32 |
| 3 | 1:388 |
| 4 | 1:97 |

These titers were at least as good as the titers obtained by the injection of fish held at 12° C.

EXAMPLE 5

This experiment was conducted to investigate the parameters of the spray pressure necessary to provide satisfactory immunization with Vibrio vaccine.

Juvenile coho salmon in groups of 60 were sprayed with the bacterin acid control at a series of pressures with a paint spray and a sandblast gun. The pressures employed were 20, 30, 40, 50, 70 and 90 psi. As a tracer, a red or yellow fluorescent dye was added to the bacterin dispersion. A pressure of 70 to 90 psi was found necessary to provide dye retention on all of the fish sprayed with the sandblaster. At these pressures the paint sprayer provided from 50 to 88% retention.

Triplicate samples of 20 fish from each group were exposed to Vibrio anguillarum challenge and 10 titers were run from each group. Table 3 below gives the geometric mean for titers and the survival rates found 5 weeks following treatment. High blood titers and survival rates were evident at all spray pressures after 5 weeks. Blood antibody titers taken on an 8 fish sample 4 weeks after the spray immunization treatment using a sandblaster with 90 psi showed a geometric mean of 279.

The fish may be vaccinated directly in dip nets on a batch basis. Alternatively they may be treated in a continuous manner by transferring the fish from one holding area to another via a trough, and having a spraying device arranged to spray the fish as they come through the trough.

We claim:

1. A method for vaccinating fish against diseases including Vibrio anguillarum, Aeromonas salmonicida, and furunculosis, comprising disposing said fish out of water by removal therefrom and into air, and spraying an antigenic composition of killed Vibrio anguillarum, or Aeromonas salmonicida, or furunculosis bacterins upon the exterior of the fish in the absence of any physical contact between said water and said fish.

2. The fish vaccinating method of claim 1 wherein the said antigenic composition is dispersed by said spraying within gaseous space separating said spray means from said fish whereby a substantial portion of said fish exterior receives said antigenic composition thereon.

3. The fish vaccinating method of claim 2 wherein said fish is directed to move through said dispersed antigenic composition whereby vaccinating said fish is in a continuous manner.

TABLE 3

Color retention, geometric mean, blood titers and survival rates for juvenile coho salmon sprayed with Vibrio anguillarum vaccine and fluorescent pigment at 20, 30, 50, 70 and 90 psi with a sandblaster and paint sprayer.

| Treatment group | Percent color retention | Geometric mean (n = 10) antibody titer (5 weeks after treatment) | Accumulative mortality 3 replicates, 20 fish each total 60 fish per group | Mean percent survival |
|---|---|---|---|---|
| Control spray (No vaccine) | 100 | 0 | 59 | 1.6 |
| Vibrio anguillarum vaccine sprayed with sandblaster at: | | | | |
| 0-1 psi | — | 32 | 0 | 100 |
| 3-5 second immersion | — | 7 | 0 | 100 |
| 20 psi | 17 | 588 | 2 | 96.6 |
| 30 psi | 66 | 1,176 | 2 | 96.6 |
| 50 psi | 53 | 388 | 0 | 100 |
| 70 psi | 100 | 1,176 | 0 | 100 |
| 90 psi | 100 | 676 | 1 | 98.3 |
| with paint sprayer at: | | | | |
| 20 psi | 39 | 1,024 | 1 | 98.3 |
| 30 psi | 60 | 891 | 1 | 98.3 |
| 50 psi | 48 | 1,024 | 0 | 100 |
| 70 psi | 50 | 588 | 2 | 96.6 |
| 90 psi | 88 | 891 | 1 | 98.3 |

In addition to the specific embodiments shown various alternatives and modifications are possible. The vaccine preparations may be modified by using different killing techniques or incubation periods. Instead of bentonite other absorbents or cation exchangers may be employed. Various adjuvants as known to the art may be included or substituted in the vaccine. The spray pressure may be varied up to a maximum which is harmful to the fish and the pattern of spray may be adjusted as appears necessary.

4. The fish vaccinating method of claim 1 wherein the antigenic composition contains a small amount of an adjuvant comprising an absorbent of the class exemplified by bentonite and an anion exchanger.

5. The fish vaccinating method of claim 1 wherein the antigenic composition contains an abrasive powder.

6. The fish vaccinating method of claim 1 wherein the spraying employs a pressure ranging up to about 90 psi.

7. The fish vaccinating method of claim 6 wherein the pressure employed is from about 70 psi to about 90 psi.

* * * * *